United States Patent [19]

Lindemann et al.

[11] 4,013,079
[45] Mar. 22, 1977

[54] MEDICAL DILATOR

[76] Inventors: Hans-Joachim Lindemann, Oderfelder Str. 6, 2 Hamburg 13; Peter P. Wiest, Gotha-Allee 19, 1 Berlin 19, both of Germany

[22] Filed: Nov. 11, 1975

[21] Appl. No.: 630,819

[30] Foreign Application Priority Data

Nov. 13, 1974 Germany ............................ 2454351

[52] U.S. Cl. ................................ 128/341; 128/361
[51] Int. Cl.² ........................................ A61M 29/00
[58] Field of Search ........ 128/4, 6, 7, 20, 242–244, 128/303 R, 303.11, 303.12, 328, 341, 343, 356, 361

[56] References Cited

UNITED STATES PATENTS

| | | | |
|---|---|---|---|
| 1,628,272 | 5/1927 | Reitz | 128/341 X |
| 1,955,863 | 4/1934 | Schmidt | 128/303.12 X |
| 2,842,133 | 7/1968 | Uhma | 128/345 |
| 3,352,303 | 11/1967 | Delaney | 128/348 X |
| 3,630,190 | 12/1971 | Baker | 128/341 X |
| 3,642,002 | 2/1972 | Otterstrom | 128/303 R X |
| 3,779,233 | 12/1973 | Saslow et al. | 128/6 |
| 3,902,499 | 9/1975 | Shene | 128/328 |

FOREIGN PATENTS OR APPLICATIONS 795,316   5/1958   United Kingdom ............... 128/343

*Primary Examiner*—Edgar S. Burr
*Assistant Examiner*—Paul T. Sewell
*Attorney, Agent, or Firm*—Max Fogiel

[57] ABSTRACT

A dilator for medical applications particularly for dilating the cervical canal of the uterus in which a rigid rod-shaped probe has a profiled head section on the free end of the probe. A housing for supporting the probe has also a vibrating arrangement for applying vibrations transversely to the longitudinal axis of the probe. The frequency and amplitude of vibration of the probe are continuously variable and independent of each other. An adjusting slide for continuous variable adjustment of the vibration frequency or amplitude, is provided on a handle located at right angles to the longitudinal axis of the probe. The vibrating arrangement within the housing is releasably connected to a power supply via a cable and quick-action couplings.

18 Claims, 11 Drawing Figures

MEDICAL DILATOR

BACKGROUND OF THE INVENTION

The present invention relates to a dilator for medical purposes, particularly for the dilation of the cervical canal of the uterus.

Dilators known in the art are cylindrical, metallic Hegar rods of different diameters. These are introduced successively into the cervical canal, starting with the Hegar rod of smallest diameter up to the Hegar rod with the required larger diameter. The use of these Hegar rods is both expensive and cumbersome. In addition, uterine cramp conditions (uterus spasmus) may make the dilation more difficult. Furthermore, there exists an increased danger of infection since several rods, which must be sterilized, have to be used. Finally, there is the danger that the thin Hegar rods may damage the mucuous membrane of the uterine wall or that the uterine wall may be perforated. The bleeding which may result could, for example, make the hysteroscopy more difficult and hence impair the diagnosis. Also, the successive insertion of various Hegar rods is very time consuming.

It is, therefore, an object of the present invention to provide a dilator for medical purposes particularly for dilating the cervical canal of the uterus in which the dilator facilitates a particularly gentle dilation within a short period of time, without the hazard of damaging the mucuous membrane of the uterine wall, and which reduces the chance for infection.

Another object of the present invention is to provide a dilator of the foregoing character which may be economically fabricated and maintained in service.

A further object of the present invention is to provide a dilator, as described, which is highly reliable in service, has a long operating life, and is simple in design and construction.

SUMMARY OF THE INVENTION

The objects of the present invention are achieved by providing a rigid rod-like probe with a profiled head section on its free end which is set into vibrations transversely to the longitudinal axis of the probe by means of a vibration device located inside a housing. This creates a dilator which makes possible a particularly gentle dilation of the cervical canal within a relatively short time. The dilator uses only one object, the probe with the profiled head section, so that the chance of infection is reduced to a minimum. The profiled head section eliminates any danger of damaging the mucuous membrane of the uterine wall and of perforating the uterine wall, so that no bleeding whatever impedes the hysteroscopy and the diagnosis. Finally, the cervical canal of the uterus is loosened by the vibrations, generated by the dilator in accordance with the present invention, and relaxed during dilation. The dilator in accordance with the present invention may be used to particular advantage during hysteroscopy and for the insertion of intra-uterine pessaries.

In accordance with a preferred embodiment of the present invention, the vibration frequency and the vibration amplitude of the probe are continuously variable, and independent of each other, by means of the vibration device. This facilitates a particular setting tailored to the needs of the particular patient. For simple handling, the housing is equipped with a handle located at right angles to the longitudinal axis of the probe. By pivoting the handle about the longitudinal axis of the probe, the plane of vibration of the probe can be rotated by ±60°. An adjusting slide for continuously varying the vibration frequency and the vibration amplitude of the probe is located on the handle. The vibration device, located inside the housing, is releasably connected to a power supply unit via a cable and quick-action couplings. Thus the dilator, for sterilizing, can be easily disconnected from the power supply unit. The vibration device consists of a magnet with windings and an armature connected to the probe. The probe is releasable connected to the armature of the vibration device, so that probes of various designs may be used.

In another preferred embodiment of the present invention, the head section of the probe has a larger cross-section than the stem section. The profiled head section is adapted to nulliparous and multiparous uteri. Accordingly, the head section may be olive-shaped, lenticular or cone-shaped, rounded-off on all sides or have the shape of a truncated cone with a cylindrical stem, being rounded-off on all sides.

In order to produce within the uterus (cavum uteri) pressure below atmospheric by means of the dilation probe (curettage), in a further embodiment of the present invention, the probe is provided with a longitudinal bore (or drill) hole, which terminates in at least one suction opening in the head section and which is closed at the other end of the probe and is provided with a cross bore (transverse drill hole), to which a flexible hose for attaching the probe to a vacuum or suction pump can be attached. The suction opening, as an extension of the longitudinal bore hole, may run straight through the head section of the probe. Also, several suction openings may be provided at an angle with the longitudinal bore in the head section. Finally, there may be several staggered suction openings whose cross-section is oval-shaped. The head section may be an integral part of the probe. However, a two-piece design is also possible where the head section, provided with one or several suction openings, is connected to the probe stem by means of a fine-pitch thread.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENT

Figure 1:
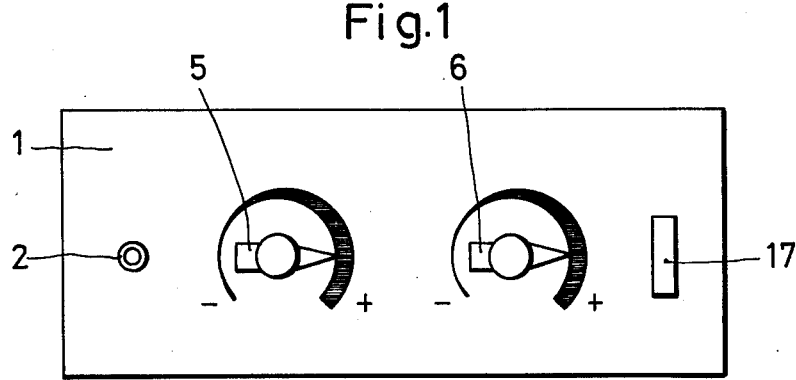
FIG. 1 is a plan view of a power supply control panel for the dilator.

A power supply 1 with a power switch 17 has an output socket 2 which can be connected via a cable 4 by means of a quick-action coupling 3 to at least two poles or terminals. In addition, the power supply has a potentiometer 5 for setting the vibration frequency, and a potentiometer 6 for setting the vibration amplitude of the signal to be picked up on the output socket 2. This signal is applied via the cable 4 and another quick-action coupling 3 to a dilator 18 via its socket 36.

The dilator 18 consists of a housing 15 for accommodating a vibration device 16, a rigid rod-like probe 9, connected thereto, with a shaped or profiled head section 10 located at the free end of the probe and a handle 7 which is located on housing 15 at right angles to the longitudinal axis of the probe 9. An adjusting slide 11 for the continuously variable adjustment of the vibration frequency and vibration amplitude of probe 9 is located on handle 7.

Figures 2, 3:
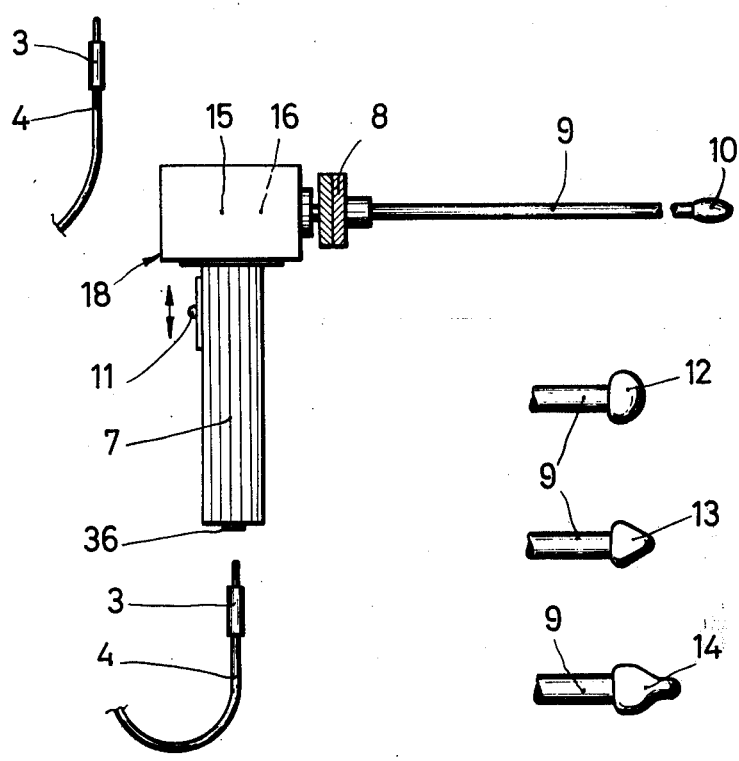
FIG. 2 is a side view of a dilator with a probe and a head section in a first embodiment.
FIG. 3 are views of head sections of the probe in various embodiments.
Figure 4:
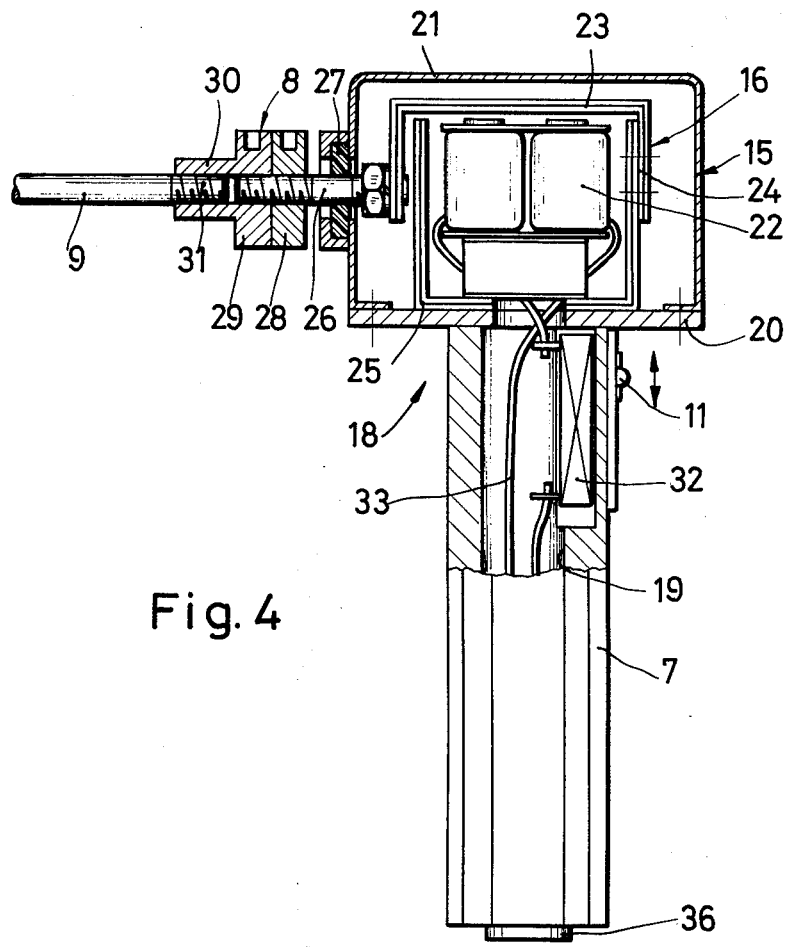
FIG. 4 shows a vertical section through the dilator in actual size.
Figure 5:
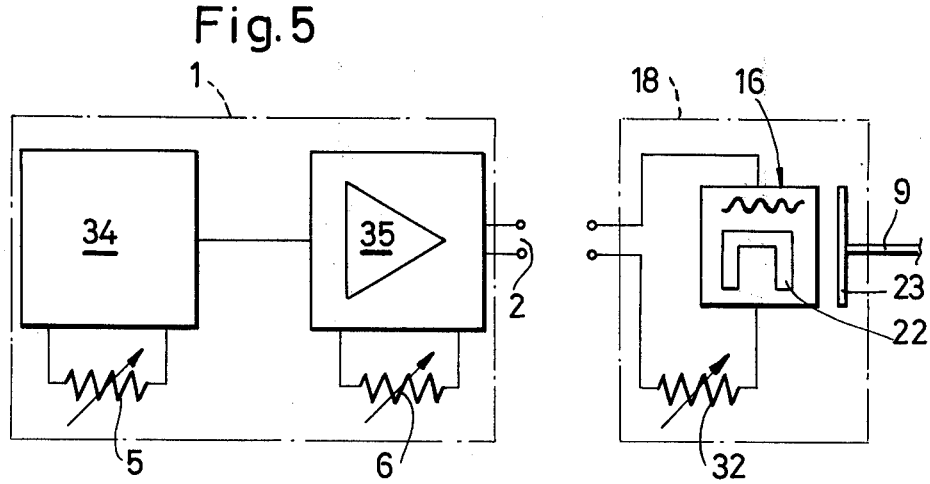
FIG. 5 is a schematic circuit diagram of the power supply device and of the dilator.

As shown in FIGS. 2 and 3, the shaped head section, for adjustment for nulliparous and multiparous uteri may be an olive-shaped head section 10, a lenticular head section 12, a cone-shaped head section 13 or a head section in the form of a truncated cone with a cylindrical stem 14. All head sections, in particular the head sections 13, 14, are rounded off on all sides. The head sections 10, 12, 13, 14 of probe 9 have a larger cross-section than the cylindrical stem. They are rigidly attached, for example, by hard-soldering (brazing). The probe 9 is connected to the vibration device 16 via a disconnectable joint 8.

The handle 7 of the dilator 18 is a cast part and provided on diametrically opposed partial surfaces of its periphery with ribs to assure a safe grip. Its relatively thick walls enclose a central opening 19. At the end, not facing the socket 36, the handle 7 has a base plate 20 which, together with a housing shell 21, constitutes the housing 15. The latter holds the vibrating device 16, consisting of a magnet 22 provided with windings and an armature 23. The U-shaped armature 23 extends over the magnet 22, which carries windings, and one of its legs in area 23 is rigidly connected with a carrier 25 enclosing the magnet 22 in a U-shaped fashion. A setscrew 26 is screwed into the free leg of the armature 23 and is held by a lock nut. The setscrew 26 passes through the housing shell 21; a silicon rubber membrane 27 is provided for sealing the housing shell. On the free-threaded portion of the setscrew 26, two shaft nuts 28, 29, constituting the disconnectable joint 8, are locked to each other. In a cylindrical shoulder 30, the shaft nut 29 accommodates a threaded portion 31 of the probe 9, which, therefore, is releasably connected to the armature 23 of the vibration device 16.

The carrier 25 enclosing the magnet 22, together with the base plate 20, is screw-fastened to the handle 7. The wall of handle 7 carries a potentiometer 32 which can be adjusted via the adjusting slide 11. A cable 33 connects one pole or terminal of socket 36 with one end of the windings of magnet 22; the other end of these windings is connected to the input of potentiometer 32 and its output is connected to the other terminal of socket 36.

The power supply unit 1 holds a power supply arrangement (transformer) with a DC output. It can be actuated via power switch 17. There also is provided a square-wave generator 34 whose frequency can be varied through potentiometer 5. Furthermore, an amplifier 35 is located inside the power supply unit 1. This amplifier amplifies the current pulses produced by the square-wave generator and can be regulated by means of potentiometer 6. The vibration frequency and the vibration amplitude of probe 9, and its head section 10 in particular, may be continuously varied by moving potentiometer 5, or potentiometer 6, respectively. The signal corresponding to the potentiometer settings is applied to the socket 2 and transmitted from there via cable 4 to the vibration device 16.

The setting for the vibration frequency and for the vibration amplitude of probe 9 can also be made by means of the adjusting slide 11. If the vibration frequency of the probe 9 is to be adjusted by means of the adjusting slide 11, the potentiometer 5 is adjusted to a setting where it is bridged by the potentiometer 32, so that the potentiometer 32, actuated by adjusting slide 11, assumes the function of the potentiometer 5 for setting the vibration frequency. In that case, the vibration amplitude is set by the potentiometer 6. On the other hand, the potentiometer 6 can be turned to a setting where it is bridged by the potentiometer 32. In this case, the vibration amplitude can be set by means of potentiometer 32, which is actuated from the adjusting slide, whereas the vibration frequency is set by means of the potentiometer 5.

When introducing the profiled and rounded-off head sections 10, 12, 13, 14 of probe 9 into the cervical canal of the female patient, the canal is carefully expanded under the influence of the head section. The vibration frequency and the vibration amplitude of the head section are set by the physician. By pivoting the dilator 18 about the longitudinal axis of probe 9 by ± 60°, the physician can rotate the plane of vibration of the head section so that the cervical canal is expanded in as circular a manner as possible. This rotation, by constructing the vibration device 16 differently, may also be accomplished by the probe 9 itself.

Figure 6:
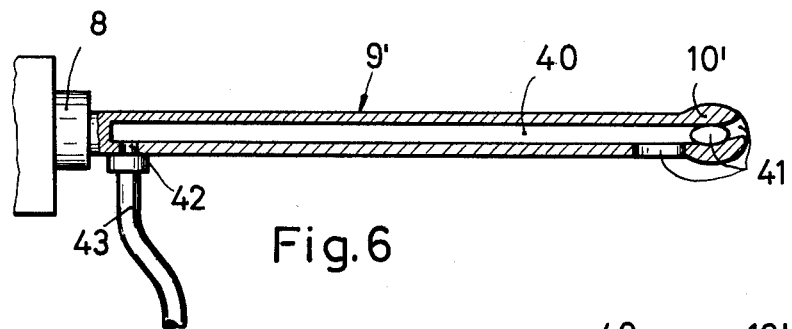
FIG. 6 shows a lengthwise section through the probe in a different embodiment on an enlarged scale.
Figure 7:
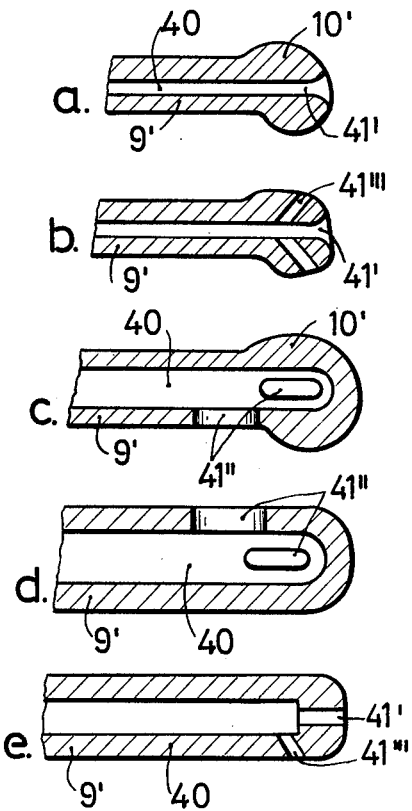
FIG. 7 a-e are sectional views showing various embodiments of the probe head section of FIG. 6.

In order to produce a partial vacuum inside the uterus (cavum uteri) by means of the dilation probe 9 (curettage), provision has been made in accordance with FIG. 6 that the probe 9' has a longitudinal bore 40 which terminates in the head section 10' in at least one suction opening 41 and which is closed on the other end of the probe 9'. It is equipped with a transverse drill hole 42 to which a flexible hose 43 for connecting the probe to a vacuum or suction pump (not shown) is attached. In accordance with FIG. 7a, the suction opening 41', as an extension of longitudinal bore 40, may run straight through the head section 10' of the probe 9. One may also provide several suction openings 41''' at an angle with the axis of the longitudinal bore 40 (FIG. 7b). Finally, one may have several, staggered suction openings 41'', whose cross-section is oval shaped (FIG. 7c and d). In FIG. 7 a through c, the head section 10' has a larger cross-section than the stem of probe 9'. In the embodiments of FIG. 7 d and e, the head section has the same diameter as the stem of probe 9'. Here also the suction openings 41 through 41''' may be provided in the head section. In designing suction openings 41' and 41''' in accordance with FIG. 7a, b and c, care must be taken that the cross-section not be too small since that might lead to clogging.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore such adaptations should and are intended to be comprehended within the meaning and range of equivalence of the following claims.

We claim:

1. A medical dilator particularly for dilating the cervical canal of the uterus comprising, in combination, a housing; a rigid elongated rod-shaped probe connected at one end to said housing and having a free end; a profiled head section on said probe and located on the free end of said probe; and means confined entirely within said housing for applying vibrations transversely to the longitudinal axis of said probe, said probe and said profiled head section being free of said means confined entirely within said housing, said probe having a substantially smaller cross-section than said housing so as to be of such size as to enable dilation of the cervical canal.

2. The dilator as defined in claim 1 including means for varying continuously the frequency and amplitude of vibration independent of each other.

3. The dilator as defined in claim 1 including a handle on said housing and located at right angles to the longitudinal axis of said probe.

4. The dilator as defined in claim 3 including an adjusting slide on said handle for varying continuously the vibration frequency or amplitude of said probe.

5. The dilator as defined in claim 1 including power supply means for supplying power to said means for applying vibrations to said probe; and cable means with quick-action coupling means for releasably connecting said vibrating means from said power supply means.

6. The dilator as defined in claim 1 wherein said means for applying vibrations transversely to said probe comprises magnet means with windings; and armature means connectable to said probe.

7. The dilator as defined in claim 6 including means for releasably connecting said probe to said armature means.

8. The dilator as defined in claim 1 including a stem section on said probe, said head section of said probe having a substantially larger cross section than said stem section.

9. The dilator as defined in claim 1 wherein said head section of said probe is olive-shaped.

10. The dilator as defined in claim 1 wherein said head section of said probe is lenticular.

11. The dilator as defined in claim 1 wherein said head section of said probe is conical and is rounded-off on all sides.

12. The dilator as defined in claim 1 wherein said head section of said probe comprises a truncated cone with a cylindrical stem rounded-off on all sides.

13. The dilator as defined in claim 1 including vacuum pump means, said probe having a longitudinal bore terminating in said head section, a transverse bore communicating with said longitudinal bore, the end of said longitudinal bore opposite said section head being closed; and flexible hose means for connecting said transverse bore to said vacuum pump means for producing pressure below atmospheric in the uterus.

14. The dilator as defined in claim 13 wherein said longitudinal bore in said probe terminates in a suction opening, said suction opening extending from said longitudinal bore and passing directly through said head section of said probe.

15. The dilator as defined in claim 13 wherein said longitudinal bore terminates in a plurality of staggered suction openings having an oval-shaped cross-section.

16. The dilator as defined in claim 13 wherein said longitudinal bore of said probe terminates in at least one suction opening inclined to the longitudinal axis of said longitudinal bore in said probe.

17. A dilator as defined in claim 1 wherein said probe comprises an elongated rod-shaped member projecting from said housing, said probe being connected to said housing at one end of said probe; said vibrations being conducted from said housing and along the length of said probe to said profiled head section, said profiled head section being displaced relative to said one end of said probe connected to said housing with selectable displacement amplitude and frequency during said vibrations, said vibrations lying substantially in a plane passing through the longitudinal axis of said probe; said housing being substantially free of said displacement amplitude, said profiled head being spaced from said housing by the length of said probe.

18. The dilator as defined in claim 1 including means for varying continuously the frequency and amplitude of vibration independent of each other; a handle on said housing and located at right angles to the longitudinal axis of said probe; and adjusting slide on said handle for varying continuously the vibration frequency or amplitude of said probe, power supply means for supplying power to said means for applying vibrations to said probe; cable means with quick-action coupling means for releasably connecting said vibrating means from said power supply means; said means for applying vibrations transversely to said probe comprising magnet means with windings and armature means connectable to said probe; means for releasably connecting said probe to said armature means; a stem section on said probe, said head section of said probe having a substantially larger cross-section than said stem section; vacuum pump means, said probe having a longitudinal bore terminating in said head section, a transverse bore communicating with said longitudinal bore, the end of each said longitudinal bore opposite said section head being closed; flexible hose means for connecting said transverse bore to said vacuum pump means for producing pressure below atmospheric in the uterus, said longitudinal bore in said probe terminating in a suction opening, said suction opening extending from said longitudinal bore and passing directly through said head section of said probe, said probe comprising an elongated rod-shaped member projecting from said housing, said probe being connected to said housing at one end of said probe, said vibrations being conducted from said housing and along the length of said probe to said head section, said head section being displaced relative to said one end of said probe connected to said housing with selectable displacement amplitude and frequency during said vibrations, said vibrations lying substantially in a plane passing through the longitudinal axis of said probe, said housing being substantially free of said displacement amplitude, said profiled head being spaced from said housing by the length of said probe.

* * * * *